(12) United States Patent
Rösel et al.

(10) Patent No.: US 6,439,038 B1
(45) Date of Patent: Aug. 27, 2002

(54) METHOD FOR MONITORING THE OPERABILITY OF A LAMBDA SENSOR

(75) Inventors: Gerd Rösel; Hong Zhang, both of Regensburg (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/127,535

(22) Filed: Jul. 31, 1998

(30) Foreign Application Priority Data

Jul. 31, 1997 (DE) .......................... 197 33 107

(51) Int. Cl.$^7$ ............................................. G01M 15/00
(52) U.S. Cl. ...................................................... 73/117.3
(58) Field of Search ........................... 73/117.2, 117.3, 73/118.1; 123/326

(56) References Cited

U.S. PATENT DOCUMENTS

| | | | |
|---|---|---|---|
| 5,438,826 A | * 8/1995 | Blischke et al. | .............. 60/276 |
| 5,444,977 A | * 8/1995 | Kawabata | .................... 60/276 |
| 5,488,858 A | * 2/1996 | Achleitner | ................. 73/118.1 |
| 5,610,321 A | * 3/1997 | Shinmoto | .................... 60/277 |
| 5,819,530 A | * 10/1998 | Asano et al. | ................. 60/277 |
| 6,171,565 B1 | * 1/2001 | Hohne et al. | ............ 423/239.1 |

FOREIGN PATENT DOCUMENTS

| | | |
|---|---|---|
| EP | 0 616 119 A1 | 9/1994 |
| EP | 0 626 506 A1 | 11/1994 |
| EP | 0 652 358 A2 | 5/1995 |

* cited by examiner

Primary Examiner—Benjamin R. Fuller
Assistant Examiner—Maurice Stevens
(74) Attorney, Agent, or Firm—Laurence A. Greenberg; Werner H. Stemer; Gregory L. Mayback (57) ABSTRACT

A method of monitoring the dynamic operability of a lambda sensor (monitor sensor), disposed in the exhaust gas stream of an internal combustion engine downstream of a catalytic converter. Once the engine operating state of overrun fuel cutoff is detected, the rich/lean switching time of the monitor sensor disposed downstream of the catalytic converter is ascertained and weighted as a function of the air flow rate (LMM) in the intake conduit. By comparing the mean value of the thus-obtained switching time with a limit value and ensuing evaluation, the operability of the monitor sensor is diagnosed. Operability is assured if the switching time is below the limit value. Other diagnostic criteria are formed by evaluating the signal level of the monitor sensor.

15 Claims, 5 Drawing Sheets

METHOD FOR MONITORING THE OPERABILITY OF A LAMBDA SENSOR

BACKGROUND OF THE INVENTION

Field of the Invention

The invention relates to a method for monitoring the dynamic operability of a lambda sensor, disposed in the exhaust gas stream of an internal combustion engine downstream of a catalytic converter.

Pollutant emissions from an internal combustion engine can be reduced by catalytic post-treatment, using a so-called three-way catalytic converter. Efficient post-treatment, however, requires a stoichiometric mixture. To that end, mixture regulation is employed, with a lambda sensor (regulating sensor) disposed upstream of the catalytic converter in the exhaust gas tract, which periodically regulates the mixture composition within narrow limits around the desired value. To that end, lambda sensors that output a high voltage when the fuel/air mixture is rich and a low voltage when the fuel/air mixture is lean are for instance used; between these voltage values, there is a voltage jump, which is characteristic for $\lambda=1$ (jump sensor).

The catalytic converter may become defective over the course of its operation, for instance from the occurrence of misfiring or from using leaded fuel by mistake. If the catalytic converter is defective, the exhaust gases are no longer detoxified, or only inadequately detoxified. To monitor the conversion capability of the catalytic converter, it is known, in addition to the lambda sensor upstream of the catalytic converter, also to dispose an oxygen sensor (monitor sensor) downstream of the catalytic converter, and to evaluate the output signals of the two sensors. For example, European Patent Disclosure EP 0 626 506 A1 proposes forming the ratio of the times within which the oxygen sensor downstream of the catalytic converter and the oxygen sensor upstream of the catalytic converter indicate a rich or a lean mixture value, respectively. The catalytic converter is adequately efficient if the lesser value of these ratio values is less than predetermined limit value.

The known methods for monitoring catalytic efficiency by evaluating the output signals of the two sensors assumes that the sensors themselves are functioning properly, so that no incorrect values, obtained from aged or poisoned sensors can affect catalytic diagnosis. It is therefore necessary to monitor the operability of the sensors as well. It is known from EP 0 616 119 A1, in a lambda sensor (precatalytic sensor) disposed upstream of the catalytic converter, to measure the switching times within which the precatalytic sensor, in the context of its jump function, switches over from a high voltage value (rich voltage) that indicates a rich mixture to a lower voltage value (lean voltage) that indicates a lean mixture. The magnitude of these switching times is a measure of the operability of the precatalytic sensor.

Another method for monitoring the dynamic operability of precatalytic lambda sensors is described in EP 0 652 358 A2. In it, the dwell times within which the lambda sensor signal indicates a rich or a lean mixture are measured. The precatalytic lambda sensor is then classified as functioning correctly if both the rich and the lean dwell times are below predetermined limit values associated with the individual dwell times.

These known monitoring methods for precatalytic sensors in the, closed lambda control loop cannot, however, readily be employed for diagnosis of monitor sensors, since because of the storage capacity of the catalytic converter, the course of the closed-loop control oscillation present upstream of the catalytic converter is more or less markedly smoothed, depending on the conversion capacity of the catalytic converter. Hence no closed-loop control oscillation that can be evaluated in this way is available; instead, there is only a more or less constant signal, which cannot be evaluated for monitoring the monitor sensor, or can be evaluated only with a large potential for error.

SUMMARY OF THE INVENTION

The object of the invention is to disclose a method with which the dynamic operability of a monitor sensor (jump sensor), which is disposed downstream of the catalytic converter and has a binary characteristic with regard to its output signal, can be monitored.

Whenever the engine enters the operating range of overrun fuel cutoff, the output signal—as a rule, an electrical voltage—of an intact monitor sensor drops very quickly from a relatively high value to a low value, because of the lean mixture that then prevails.

Once the engine operating state of overrun fuel cutoff is detected, the rich/lean switching time of the monitor sensor is therefore ascertained and weighted as a function of the air flow rate and the intake system. By comparison of the mean value of the switching time thus obtained with a limit value and ensuing evaluation, the operability of the monitor sensor is diagnosed. The operability is assured if the switching time is below the limit value.

By monitoring the output signal of the monitor sensor upon entering and leaving the overrun fuel cutoff phase, implausible voltage values from an extreme lengthening of the switching times, as well as breaks in the signal line of the sensor, can be detected. The advantage attainable with the invention is in particular that with the method described, it is easily possible to detect poisoning as well as effects of aging of the lambda sensor downstream of the catalytic converter, which can lead to a worsening in the exhaust gas values of the engine or to incorrect values in catalytic diagnosis. These worsened values can be ascribed to serious changes in the dynamic behavior of the monitor sensor (prolongation of the rise times from rich to lean and lean to rich, defective conversion behavior of the catalytic converter after the overrun fuel cutoff phase, or electrical errors (line breakage)

Other features which are considered as characteristic for the invention are set forth in the appended claims.

Although the invention is illustrated and described herein as embodied in a method for monitoring the operability of a lambda sensor, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DESCRIPTION OF THE PREFERRED EMBODIMENTS

Figure 1:
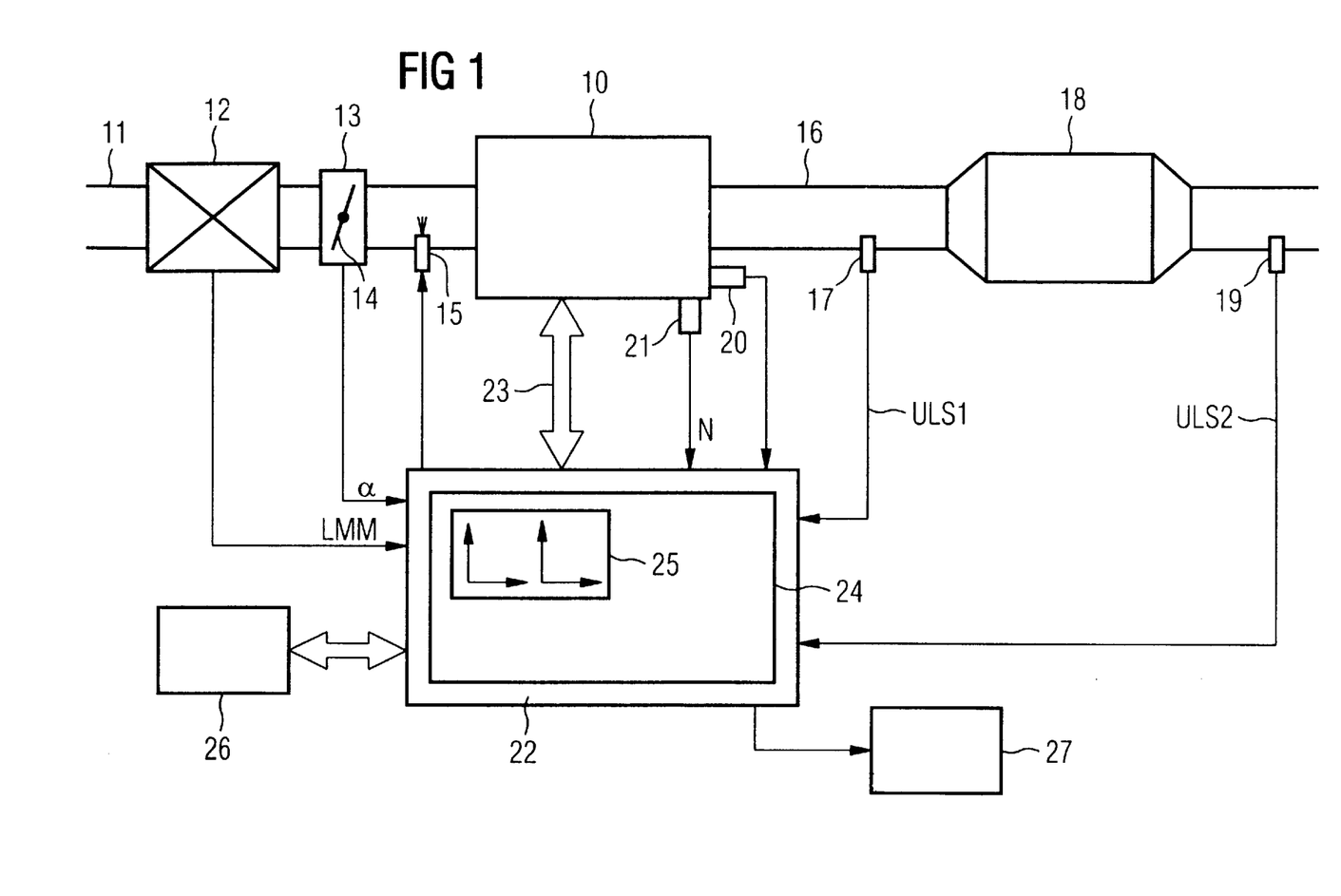
FIG. 1 shows a schematic illustration of an internal combustion engine with a monitor sensor.

FIG. 1, in the form of a block circuit diagram, shows an arrangement in which the method of the invention is employed. Only those components necessary for comprehension of the invention are shown.

The internal combustion engine 10 is supplied with an air/fuel mixture via an intake conduit 11. In the intake conduit 11, in the order of the flow direction of the aspirated air, an air flow rate meter 12, a throttle valve block 13 having a throttle valve 14 and a throttle valve sensor, not shown, for detecting the opening angle of the throttle valve 14, and a second set of injection valves 15 corresponding in number to the number of cylinders, are provided, only one of the injection valves being shown. The method of the invention can, however, also be employed in an engine that has only a single injection valve in the intake conduit (single-point or central injection), or in which the fuel is injected directly into the various cylinders (direct injection). On the outlet side, the engine 10 communicates with an exhaust gas conduit 16. Provided in the exhaust gas conduit 16, in the order of the flow direction of the exhaust gas, are a first lambda sensor 17, a three-way catalytic converter 18 serving to convert pollutant components in the exhaust gas, and a second lambda sensor 19. With the aid of the first lambda sensor 17 (regulating sensor), the fuel-air ratio in the exhaust gas upstream of the catalytic converter 18 is determined. The second lambda sensor 19 (monitor sensor) serves, among other functions, to monitor the catalytic converter 18. So-called binary lambda sensors, which for an air ratio of $\lambda=1$ have a jump characteristic with regard to their output signal, are used as the lambda sensors 17, 19.

Among other elements, a temperature sensor 20, for detecting the temperature of the engine 10 or a temperature proportional to the engine temperature, preferably that of the coolant, and an rpm sensor 21, for detecting the rpm N of the engine 10, are disposed at suitable points of the engine 10.

The output signal LMM of the air flow rate meter 12, the signal of the throttle valve sensor, the signals ULS1 and ULS2 of the lambda sensors 17, 19, the signal N of the rpm sensor 21, and the signal of the temperature sensor 20 are delivered over suitable connecting lines to a central control unit 22.

For controlling and regulating the engine 10, that is, for open- and closed-loop control thereof, the control unit 22 is connected to further sensors and actuators as well, via a data and control line 23 shown merely schematically. The control unit 22 evaluates the sensor signals and among other processes controls the injection, ignition, and diagnostic process for exhaust gas-relevant components, especially the monitoring of the lambda sensors 17, 19 and of the catalytic converter 18.

In a known way, the electronic control unit 22 has a microcomputer 24, appropriate interfaces for signal processing circuits, and an input and output unit. The microcomputer 24 includes a central processing unit (CPU), which performs the arithmetic and logical operations with the data that have been input. The programs and desired data required for this are furnished by a read only memory (ROM), in which all the program routines and all the characteristic data, characteristic curves, desired values, and so forth are stored permanently. In particular, a memory 25 is provided, in which among other things a plurality of characteristic curves and performance graphs and threshold values are stored, whose significance will be explained in further detail in conjunction with later drawing figures. An operating data memory (RAM) serves, among other purposes, to store the data furnished by the sensors until they are called up by the microcomputer 24 or are replaced with more-current data or in other words overwritten. Via a bus, all these units named are supplied with data, memory addresses and control signals. An error memory 26 is also provided, into which negative outcomes of diagnosis are written and read out at the next visit to the workshop. An indicator unit 27 connected to the control unit 22 serves to indicate the outcome of monitoring visually and/or acoustically to the driver of the vehicle driven by the engine 10.

The method evaluates the signal of the monitor sensor 19 downstream of the catalytic converter 18 during the overrun fuel cutoff phase.

Figure 2:
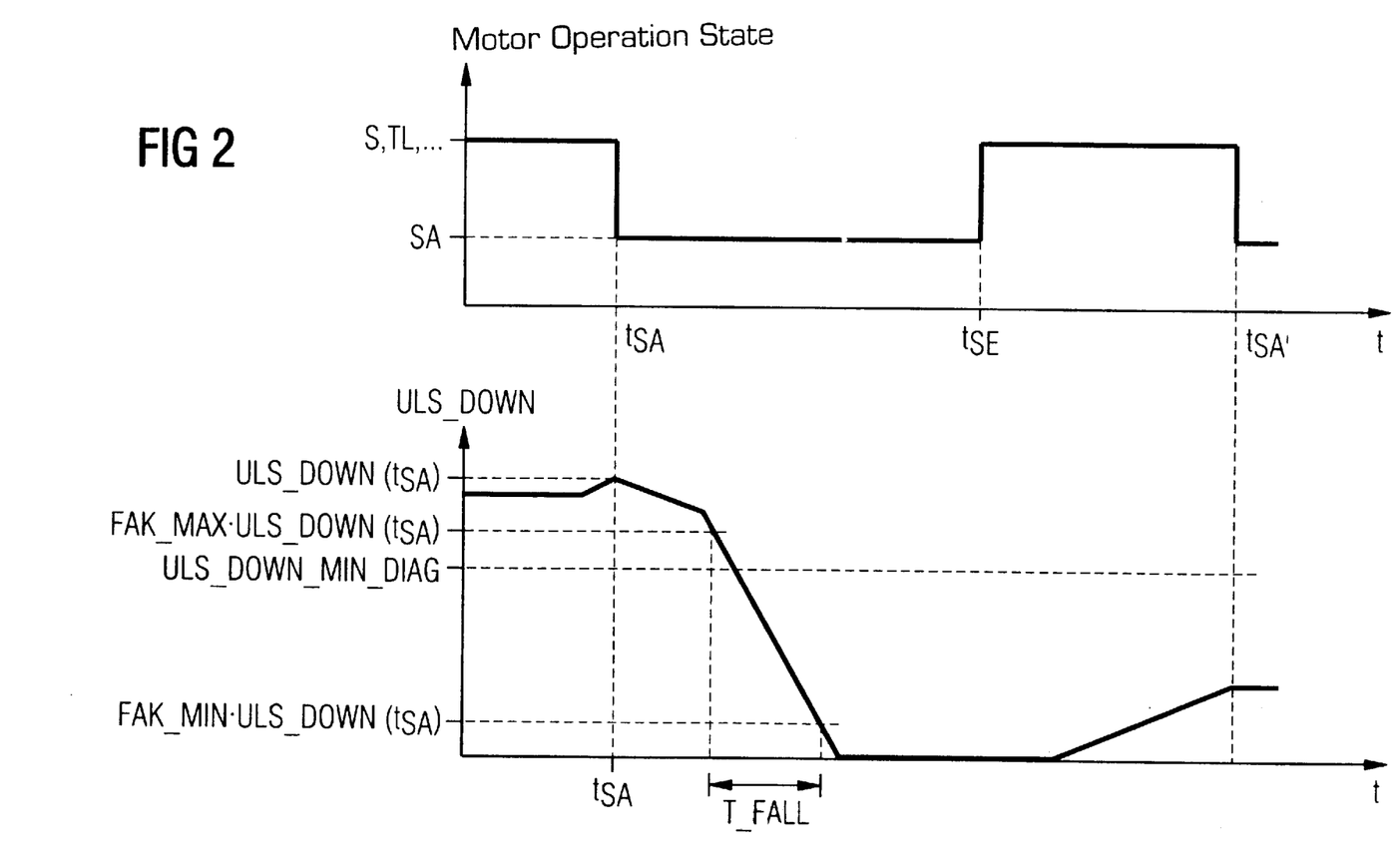
FIG. 2 shows a graph showing the course over time of the sensor voltage upon entering the overrun fuel cutoff phase.

In the upper portion of FIG. 2, in the form of a timing diagram, various engine operating states are shown. At time $t=t_{SA}$, an operating state change occurs, for instance from partial load TL or overrunning S to the overrun fuel cutoff phase SA. At time $t=t_{SE}$, the operating state of overrun fuel cutoff is left again, and at time $t=t_{SA}'$, overrun fuel cutoff again prevails.

In the lower portion of FIG. 2, the course over time of the output signal ULS_DOWN of the monitor sensor 19 during this change of operating state is shown. The value of the output signal at time $t=t_{SA}$ is indicated as ULS_DOWN $(t_{SA})$. Three threshold values are also plotted on the ordinate of this graph, namely a diagnostic threshold value ULS_DOWN_MIN_DIAG, and two threshold values that result by multiplying the output signal ULS_DOWN($t_{SA}$) by the factors FAK_MIN, FAK_MAX. The sensor switching time is designated as T_FALL and is defined as the time within which the sensor signal ULS_DOWN drops from the value FAK_MAX * ULS_DOWN($t_{SA}$) to the value FAK_MIN * ULS_DOWN($t_{SA}$).

It will now be explained in terms of FIG. 3 how the rich/lean switching time is determined and utilized for diagnosis of the monitor sensor 19.

In a first method step S3.1, the question is asked whether predetermined diagnostic conditions are met. In particular, the question is asked whether the monitor sensor 19 and the catalytic converter 18 are ready for operation. This can be done by evaluating the temperatures of the respective components. If these conditions are not met, then appropriate diagnosis cannot be begun, and the interrogation is repeated in a loop; otherwise, in method step S3.2, the question is asked, for instance by evaluating the rpm N and the opening angle of the throttle valve 14, whether the overrun fuel cutoff operating state is present. This is so whenever the rpm is above a defined threshold value and at the same time the opening angle of the throttle valve is below an applicable value.

If the overrun fuel cutoff operating state is not present, then a return is made to the start of the method (method step S3.1); otherwise, at the instant of overrun fuel cutoff $t=t_{SA}$ in method step S3.3, the value then occurring for the output signal ULS_DOWN ($t_{SA}$) of the monitor sensor 19 is detected.

To increase the replicability of the outcomes of diagnosis, the determination of the switching time T_FALL of the monitor sensor 19 is performed only whenever the voltage ULS_DOWN ($t_{SA}$), at the instant of activation $t_{SA}$ of the overrun fuel cutoff is above a diagnostic threshold value ULS_DOWN_MIN_DIAG (method step S3.4). This threshold value is defined applicably, for instance being ascertained on the engine test bench. If the voltage at the instant of activation of the overrun fuel cutoff is below this threshold value ULS_DOWN_MIN_DIAG, as is the case at time $t_{SA}$ in FIG. 2, then once again a return is made to the method start. However, if it is above the diagnostic threshold value (time $t_{SA}$ in FIG. 2), then the rich/lean switching time is ascertained in method step S3.5.

The switching time, T_FALL, for the monitor sensor 19 is determined via the period of time within which, the sensor voltage ULS_DOWN, adheres to the relation:

(FAK_MIN)*(ULS_DOWN($t_{SA}$))≦ULS_DOWN≦( FAK_MAX)*(ULS_DOWN($t_{SA}$).

The factors FAK_MIN and FAK_MAX are defined applicably; for FAK_MIN, a value of 0.1 corresponding to 10% of the value ULS_DOWN ($t_{SA}$), is advantageous, and for FAK_MAX a value of 0.9, corresponding to 90% of the value ULS_DOWN ($t_{SA}$), is advantageous.

The determination of the sensor switching time is discontinued if the operating state of overrun fuel cutoff is interrupted. As a result, it is attained that the diagnosis is performed only in the presence of a continuously dropping signal.

Because of the dependency of the switching time of the monitor sensor 19 on the air flow rate LMM in the overrun fuel cutoff phase, the value for the switching time T_FALL is normalized. The normalizing factor FAK_ULS_DOWN_FALL may be determined for instance as a function of the air flow rate in the overrun fuel cutoff phase, especially as a function of the minimum value for the air flow rate in the overrun fuel cutoff phases, or as a function of the mean value of the air flow rate during the entire overrun fuel cutoff phase. This functional relationship is preferably stored in memory in a performance graph of the memory 25 of the control unit 22 (FIG. 1).

The normalization of the sensor switching time T_FALL measured at the time $t_i$ is done in order to take into account the flow rate influence in method step S3.6, by means of the following equation:

$$T\_FALL\_NORMALIZED(t_i) = \frac{T\_FALL(t_i)}{FAK\_ULS\_DOWN\_FALL}$$

Because of the variance of the sensor switching times at an operating point, a mean value formation is then performed (method step S3.7). This mean value formation may for instance be done by way of a certain number of valid diagnosis measurements of T_FALL. The number of valid diagnosis measurements is represented by the number ANZ_ULS_DOWN_DIAG. A sum of T_FALL is then calculated. A preferred calculation of the sum of T_FALL can be performed according to the equation:

ΣT_FALL($t_{i+1}$)=ΣT_FALL($t_i$)+T_FALL_NORMALIZED($t_i$)

A mean value is then defined and calculated according to the equation:

$$T\_FALL\_MEANVALUE = \frac{\sum T\_FALL(t_{i+1})}{ANZ\_ULS\_DOWN\_DIAG}$$

In method step S3.8, the question is asked whether the number of valid diagnosis measurements ANZ_ULS_DOWN_DIAG has exceeded an applicably predetermined limit value. If this condition has not yet been met, then the method proceeds to method step S3.1, and otherwise to method step S3.9.

Once a certain number of valid diagnosis values have been ascertained, the averaged switching time T_FALL_MEANVALUE is compared in method step S3.9 with a limit value T_FALL_MAX. This value is defined applicably and is stored in the memory 25 of the control unit 22. If the ascertained switching time is below the limit value, then it is concluded that the monitor sensor 19 is operational (method step S3.10); if not, a corresponding entry "monitor sensor defective" is made in an error memory 26 of the control unit 22 of the engine (method step S3.11).

The method described for determining and evaluating the switching time of the monitor sensor 19 is used to monitor whether the dynamic behavior of the monitor sensor 19 meets certain conditions. The method is started over again if the engine 10 returns to the overrun fuel cutoff phase and the diagnostic criterion in method step S3.4 is met. The counter for the number of valid diagnosis outcomes per overrun fuel cutoff phase is reset to zero beforehand.

On entry into the operating state of overrun fuel cutoff, an output voltage which indicates a lean mixture must come to be established after a certain time, if the monitor sensor 19 is intact. Implausible voltage values, both on entering and on leaving the overrun fuel cutoff phase, from extreme prolongation of the switching times of the monitor sensor 19 (which cannot be detected by the method for determining the switching times, because the lower threshold value is never reached), as well as breaks in the signal line of the monitor sensor can be detected by monitoring the output voltage at the respective transition. Moreover, poor conversion behavior of the catalytic converter 18 after the overrun fuel cutoff phase has elapsed can also be detected.

Figure 4:
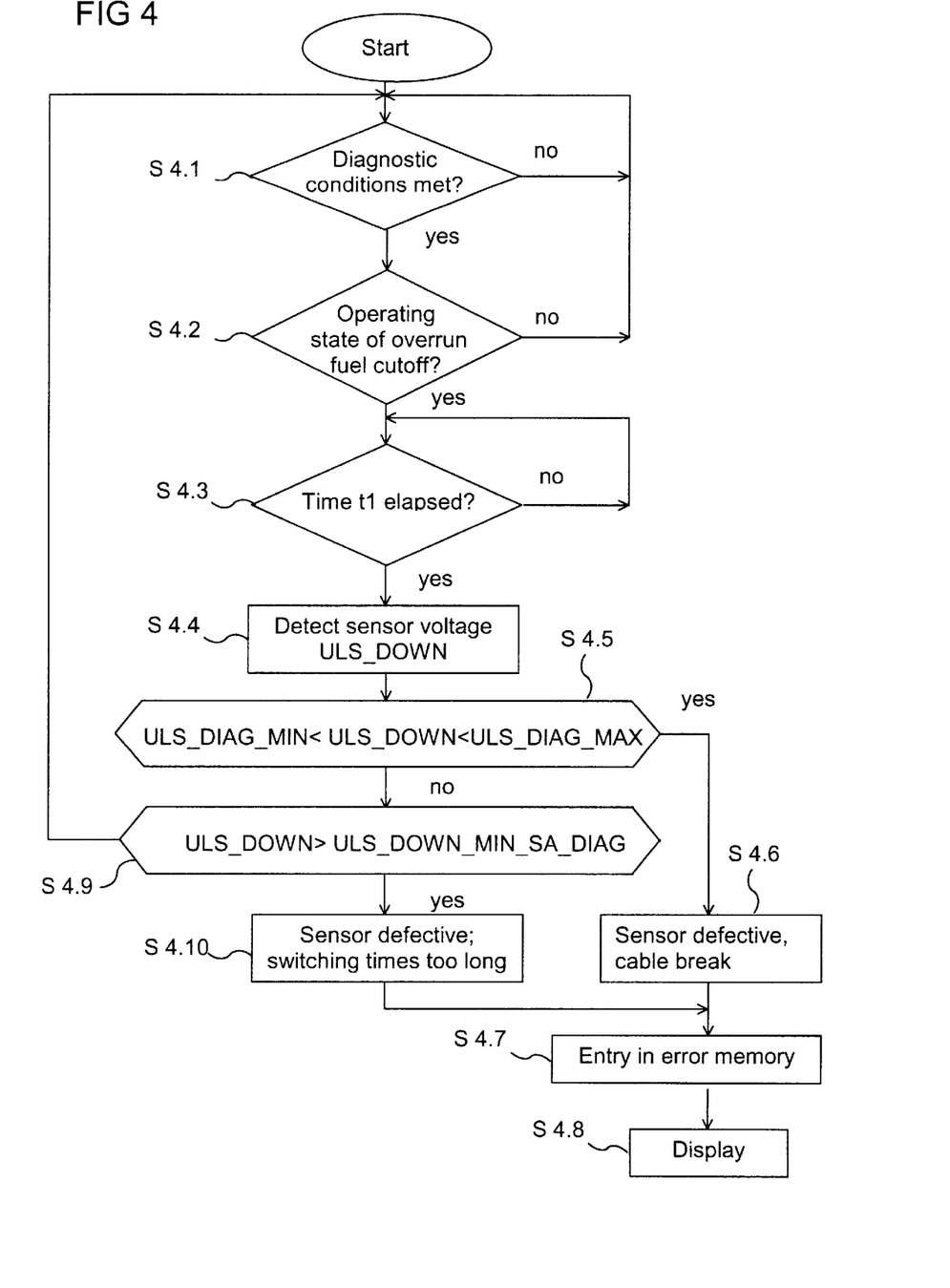
FIG. 4 shows a flowchart for monitoring and evaluating the sensor voltage upon entering the overrun fuel cutoff phase.

It will now be explained in terms of FIG. 4 how the sensor voltage is monitored and evaluated upon entering the overrun fuel cutoff phase.

Figure 3:
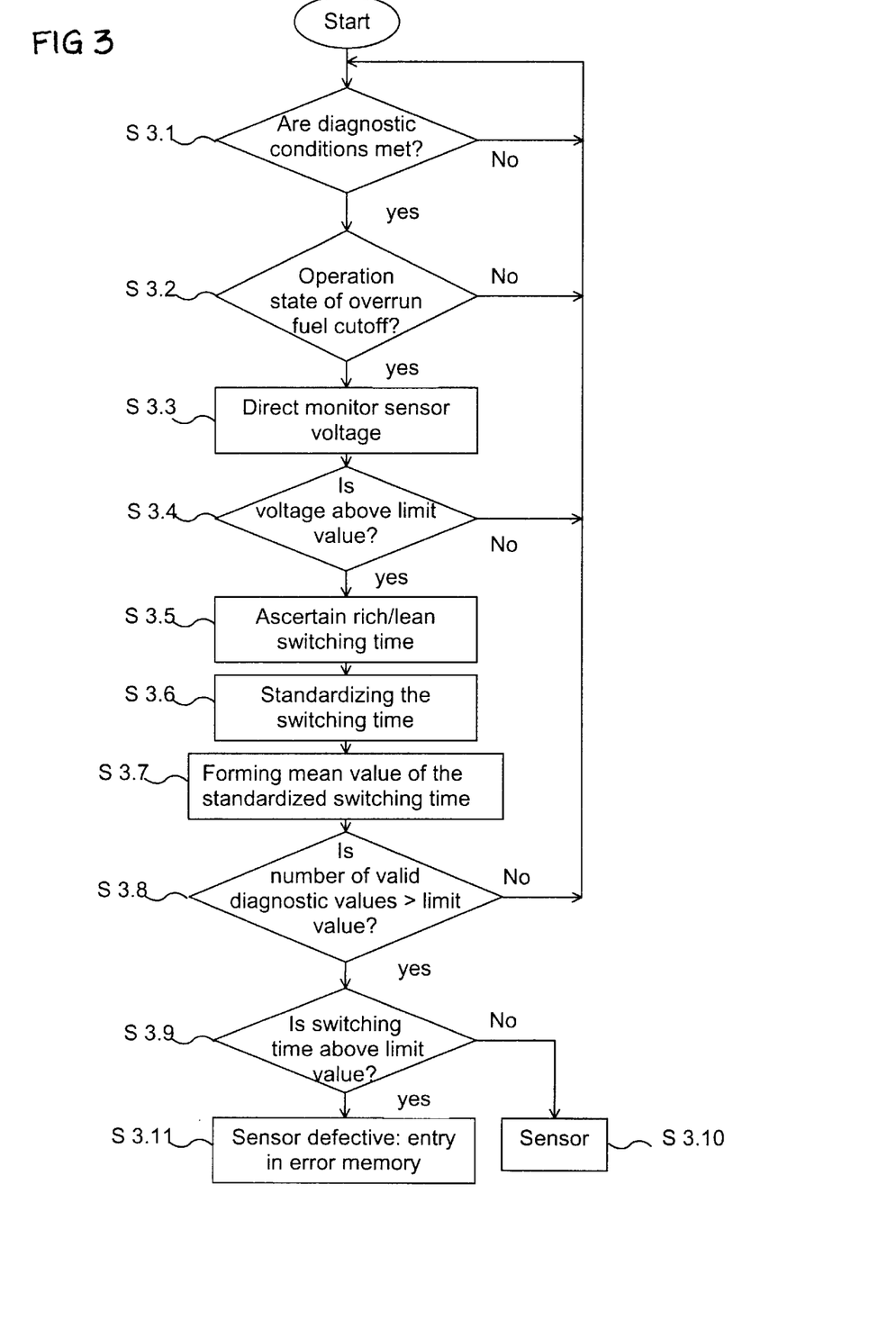
FIG. 3 shows a flowchart for monitoring and evaluating the rich/lean switching time in the overrun fuel cutoff phase.

The first method steps S4.1 and S4.2 are identical to the method steps S3.1 and S3.2 of FIG. 3. If the diagnostic conditions are met and if the operating state of overrun fuel cutoff is present, then once an operating-point-dependent time $t_1$ after entry into the overrun fuel cutoff phase has elapsed, the value of the output signal of the monitor sensor 19 must change. In error-free operation, the output voltage must then assume a value that represents a lean mixture.

The time period t1 is stored, for instance as a function of the air flow rate, in a performance graph inside the memory 25 of the control unit 22. The value of an integral for the air flow rate can thus be evaluated, or in other words compared with a predetermined threshold value. The value for the air flow rate can either be obtained directly from an air flow rate meter or ascertained by modeling, using the intake tube pressure as the input variable.

In method step S4.3, the question is asked whether this operating-point-dependent time t1 has elapsed. If this condition has not yet been met, then the interrogation repeats in a loop; otherwise, the overrun fuel cutoff was activated for the predetermined time, and in method step S4.4 the value of the sensor voltage ULS_DOWN is detected. The instant of detection is designated as the instant of diagnosis.

In method step S4.5, the question is asked whether the sensor voltage measured at the instant of diagnosis, is located between experimentally predetermined thresholds according to the relationship ULS_DIAG_MIN<ULS_DOWN<ULS_DIAG_MAX. If so, then in method step S4.6, it is concluded that the cable of the monitor sensor has broken; this error is entered in the error memory 26 (method step S4.7), and the driver of the vehicle equipped with the engine is informed acoustically and/or visually that a defect in an exhaust gas-relevant component has occurred (method step S4.8).

If the aforementioned diagnosis (cable breakage) is inapplicable and if the voltage for the monitor sensor ULS_DOWN measured at the instant of diagnosis is above an experimentally predetermined threshold ULS_DOWN_MIN_SA_DIAG (interrogation in method step S4.9, then the sensor switching time is too long; that is, the dynamic behavior of the monitor sensor is outside predetermined limits, and the method is continued with steps S4.7 and 34.8. However, if the interrogation in method step S4.9 has a negative outcome, then a return to the method start is made.

Once the engine 10 has left the overrun fuel cutoff operating state, the state of the monitor sensor 19 must change again once an operating-point-dependent time period t2 has elapsed; that is, if the monitor sensor 19 is functional, its output signal must move away from the lean stop. To determine this operating-point-dependent time t2, it is possible, for instance analogously to the determination of the time period t1, for the value of a flow rate integral, which is started after leaving the overrun fuel cutoff phase, to be compared with a threshold value. Once the overrun fuel cutoff has been deactivated for the requisite amount of time, the following diagnosis can be performed, which will now be explained in conjunction with FIG. 5.

Figure 5:
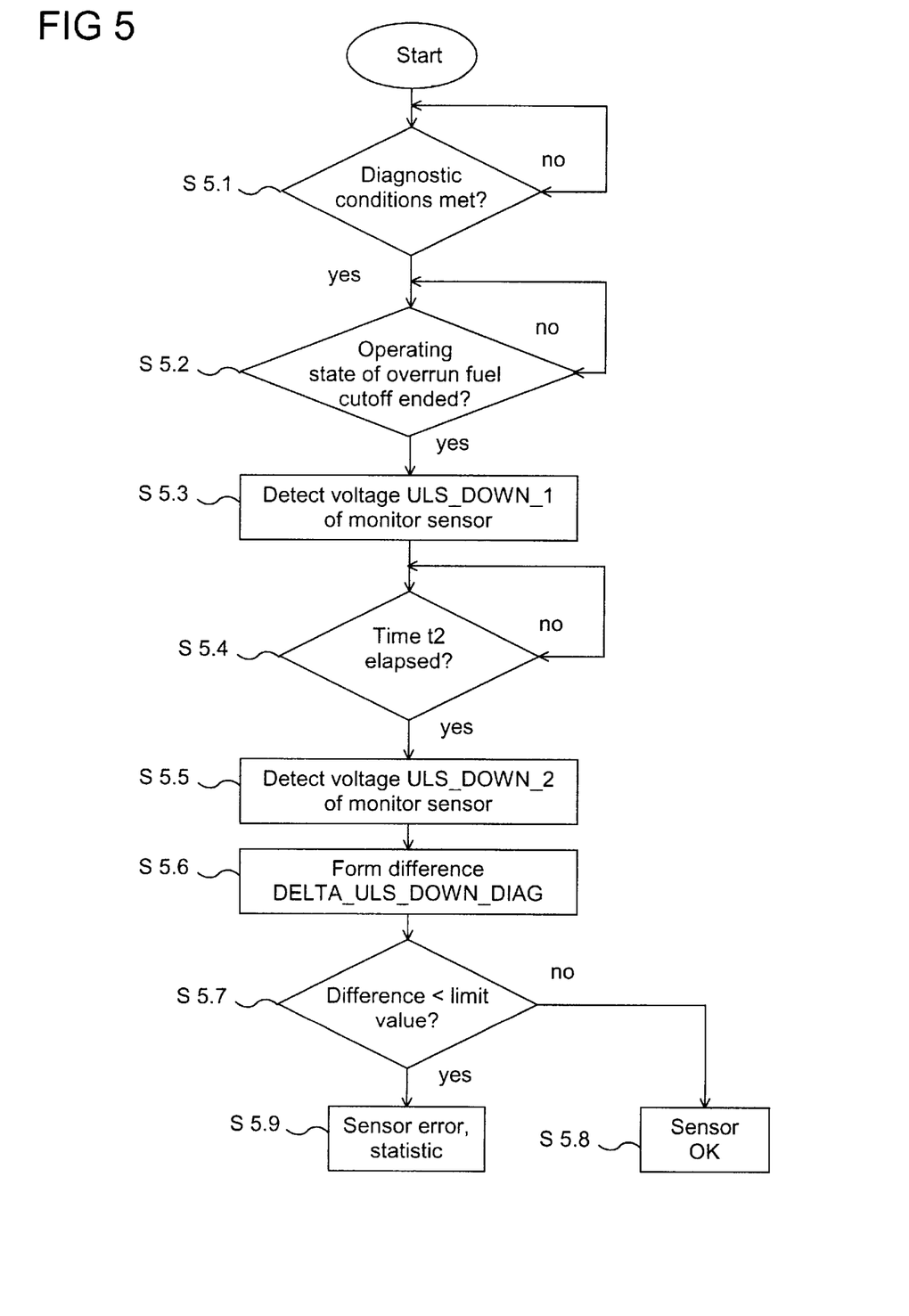
FIG. 5 shows a flow chart for monitoring and evaluating the sensor voltage upon leaving the overrun fuel cutoff phase.

The first method step S5.1 is identical to method steps S3.1 and S4.1 of the methods already described. Next, in method step S5.2, the question is asked whether the operating state of overrun fuel cutoff is at an end. This can be done again by evaluating the engine rpm and the throttle valve angle. If the engine is no longer in the overrun fuel cutoff phase, then a time counter for the time t2 is started, and in method step S5.3, a first value ULS_DOWN_1 for the output voltage of the monitor sensor is detected.

In method step S5.4, the question is constantly asked whether the time period t2 has already elapsed. If so, then at this instant the value for the output voltage ULS_DOWN_2 of the monitor sensor is detected. Next, from the two values ULS_DOWN_1 and ULS_DOWN_2, the difference DELTA_ULS_DOWN_DIAG=ULS_DOWN_1–ULS_DOWN_2 is formed (method step S5.6), and this difference is compared (method step S5.7) with a predetermined limit value DELTA_ULS_DOWN_DIAG_MIN.

If the relationship:
DELTA_ULS_DOWN_DIAG<DELTA_ULS_DOWN_DIAG_MIN (method step S5.7) is met for the difference DELTA_ULS_DOWN_DIAG between the voltage value ULS_DOWN_1 of the monitor sensor at the instant of leaving the overrun fuel cutoff phase and the voltage value ULS_DOWN_2 of the monitor sensor after the time period t2 has elapsed, or in other words at the instant at which the air flow rate for instance exceeds a defined value, then an error has occurred. However, this does not immediately lead to an entry in the error memory; instead, an error treatment is performed using a statistical evaluation (method step S5.9). Only if the error occurs repeatedly is a corresponding entry made in the error memory. However, if the difference formed in method step S5.5 is greater than the aforementioned limit value, then the conclusion is drawn in method step S5.8 that the monitor sensor is intact.

We claim:

1. In a method for monitoring the operability of a lambda sensor disposed downstream from a catalytic converter of an internal combustion engine for providing an output signal, the method which comprises the steps of:
   determining when the internal combustion engine is operating in a state of overrun fuel cutoff;
   determining, during the state of overrun fuel cutoff of the internal combustion engine, at least one switching time of the lambda sensor disposed downstream from the catalytic converter of the internal combustion engine by measuring the output signal of the lambda sensor disposed downstream from the catalytic converter; and
   normalizing the switching time with a factor, the factor determined as a function of an air flow rate delivered to the engine; and
   determining the operability of the lambda sensor disposed downstream from the catalytic converter by comparing the normalized switching time with a limit value.

2. The method according to claim 1, which further comprises:
   inputting an error into an error memory and at least temporarily indicating an error, if the lambda sensor disposed downstream from the catalytic converter is determined to be inoperative.

3. The method according to claim 2, wherein the error is indicated visually.

4. The method according to claim 2, wherein the error is indicated acoustically.

5. The method according to claim 1, which further comprises storing the factor in a performance graph of a memory of a control unit for an internal combustion engine.

6. In a method for monitoring the operability of a lambda sensor disposed downstream from a catalytic converter of an internal combustion engine for providing an output signal, the method which comprises the steps of:
   determining when the internal combustion engine is operating in a state of overrun fuel cutoff;
   detecting, during the state of overrun fuel cutoff of the internal combustion engine, the output signal of the lambda sensor disposed downstream from the catalytic converter of the internal combustion engine; and
   if the output signal exceeds a diagnostic threshold value; then
   determining at least one switching time of the lambda sensor disposed downstream from the catalytic converter by measuring the output signal of the lambda sensor disposed downstream from the catalytic converter;
   normalizing the switching time with a factor, the factor determined as a function of an air flow rate delivered to the internal combustion engine; and
   determining the operability of the lambda sensor disposed downstream from the catalytic converter by comparing the normalized switching time with a limit value.

7. The method according to claim 6, wherein the output signal is detected at an instant of activation of the state of overrun fuel cutoff.

8. In a method for monitoring the operability of a lambda sensor disposed downstream from a catalytic converter of an internal combustion engine for providing an output signal, the method which comprises the steps of:

determining when the internal combustion engine is operating in a state of overrun fuel cutoff;

determining, during the state of overrun fuel cutoff of the internal combustion engine, at least a predetermined number of switching times of the lambda sensor disposed downstream from the catalytic converter of the internal combustion engine by measuring the output signal of the lambda sensor disposed downstream from the catalytic converter;

normalizing at least the predetermined number of switching times with a factor, the factor determined as a function of an air flow rate delivered to the internal combustion engine;

calculating a mean value from the normalized predetermined number of switching times; and determining the operability of the lambda sensor by comparing the mean value with a limit value.

9. In a method for monitoring the operability of a lambda sensor disposed downstream from a catalytic converter of an internal combustion engine for providing an output signal, the method which comprises the steps of:

determining when the internal combustion engine is operating in a state of overrun fuel cutoff;

detecting, during the state of overrun fuel cutoff of the internal combustion engine, the output signal of the lambda sensor disposed downstream from the catalytic converter of the internal combustion engine; and if the output signal exceeds a diagnostic threshold value, then:

determining at least a predetermined number of switching times of the lambda sensor disposed downstream from the catalytic converter by measuring the output signal of the lambda sensor disposed downstream from the catalytic converter;

normalizing at least the predetermined number of switching times with a factor, the factor determined as a function of an air flow rate delivered to the internal combustion engine;

calculating a mean value from the normalized predetermined number of switching times; and determining the operability of the lambda sensor by comparing the mean value with a limit value.

10. In a method for monitoring the operability of a lambda sensor disposed downstream from a catalytic converter of an internal combustion engine for providing an output signal, the method which comprises the steps of:

determining when the internal combustion engine is operating in a state of overrun fuel cutoff;

determining, during the state of overrun fuel cutoff of the internal combustion engine, at least one switching time of the lambda sensor disposed downstream from the catalytic converter of the internal combustion engine by measuring the output signal of the lambda sensor disposed downstream from the catalytic converter; and discontinuing determining the switching time if it is determined that the internal combustion engine has exited the state of overrun fuel cutoff.

11. In a method for monitoring the operability of a lambda sensor disposed downstream from a catalytic converter of an internal combustion engine for providing an output signal, the method which comprises the steps of:

determining when the internal combustion engine is operating in a state of overrun fuel cutoff;

monitoring the output signal of the lambda sensor disposed downstream from the catalytic converter of the internal combustion engine upon entering an overrun fuel cutoff phase and upon leaving the overrun fuel phase; and determining that the lambda sensor is defective if an implausible course of the output signal occurs.

12. The method according to claim 11, which further comprises:

after the internal combustion engine has entered the state of overrun fuel cutoff, starting a time counter having a time period dependent on the engine operating point;

after the time period elapses, monitoring the output signal of the lambda signal;

diagnosing a cable break if the output signal is between a first and a second predetermined value; and concluding that the switching time of the lambda sensor disposed downstream from the catalytic converter is impermissibly high if the output signal is above a third predetermined value.

13. The method according to claim 12, which further comprises:

starting an air flow rate integral after leaving the point of the overrun fuel cutoff phase; and determining the time period by comparing the air flow rate integral with a predetermined threshold value.

14. The method according to claim 13, which further comprises:

starting an air flow rate integral after leaving the point of the overrun fuel cutoff phase; and determining the time period by comparing the air flow rate integral with a predetermined threshold value.

15. The method according to claim 11, which further comprises:

immediately after the internal combustion engine has exited the state of overrun fuel cutoff, starting a time counter having a time period dependent on the internal combustion engine operating point, and taking a first measurement of the output signal of the lambda sensor disposed downstream from the catalytic converter;

after the time period elapses, taking a second measurement of the output signal of the lambda signal;

calculating a difference between the first and second measurements of the output signal; and recognizing a sensor error if the difference exceeds a predetermined limit value.

\* \* \* \* \*